United States Patent

Webber et al.

[11] Patent Number: 6,152,134
[45] Date of Patent: *Nov. 28, 2000

[54] OXYGEN CONSERVING DEVICE

[75] Inventors: Stephanie J. Webber, Bainbridge; Todd Spiegelberg, Elyria; Dave Nuttall, Amherst; Anna Marsillo, Brunswick; Mike Dziak, Lorain, all of Ohio

[73] Assignee: Invacare Corporation, Elyria, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 09/051,787
[22] PCT Filed: Oct. 18, 1996
[86] PCT No.: PCT/US96/16623
  § 371 Date: Jun. 22, 1998
  § 102(e) Date: Jun. 22, 1998
[87] PCT Pub. No.: WO97/14463
  PCT Pub. Date: Apr. 24, 1997
[51] Int. Cl.⁷ ........................................ A62B 9/02
[52] U.S. Cl. ................... 128/205.24; 128/204.18; 128/204.21; 128/204.23; 128/204.26; 128/205.22
[58] Field of Search ............... 128/205.24, 205.22, 128/205.25, 204.18, 204.23, 204.24, 204.26, 204.21

[56] References Cited

U.S. PATENT DOCUMENTS

| | | | |
|---|---|---|---|
| 3,794,026 | 2/1974 | Jacobs | 128/204.18 |
| 3,905,362 | 9/1975 | Eyrick et al. | 128/204.18 |
| 3,905,363 | 9/1975 | Dudley | 128/204.18 |
| 3,923,056 | 12/1975 | Bingmann et al. | . |
| 4,029,120 | 6/1977 | Christianson | 137/494 |
| 4,096,858 | 6/1978 | Eyrick et al. | 128/204.18 |
| 4,127,129 | 11/1978 | Cramer | 128/204.18 |
| 4,168,706 | 9/1979 | Lovell | 128/204.18 |
| 4,182,599 | 1/1980 | Eyrick et al. | 417/328 |
| 4,204,536 | 5/1980 | Albarda | 128/204.22 |
| 4,323,064 | 4/1982 | Hoenig et al. | 128/204.21 |
| 4,462,398 | 7/1984 | Durkan et al. | . |
| 4,570,631 | 2/1986 | Durkan | . |
| 4,648,395 | 3/1987 | Sato et al. | . |
| 4,681,099 | 7/1987 | Sato et al. | . |
| 4,686,974 | 8/1987 | Sato et al. | . |
| 4,706,664 | 11/1987 | Snook et al. | 128/204.23 |
| 4,791,922 | 12/1988 | Lindsay-Scott et al. | 128/205.28 |
| 4,823,788 | 4/1989 | Smith et al. | 128/205.24 |
| 4,873,971 | 10/1989 | Perkins | . |
| 4,932,402 | 6/1990 | Snook et al. | . |
| 5,005,570 | 4/1991 | Perkins | 128/204.23 |
| 5,038,770 | 8/1991 | Perkins | . |
| 5,099,837 | 3/1992 | Russel, Sr. et al. | 128/204.26 |
| 5,183,037 | 2/1993 | Dearman | 128/204.18 |
| 5,211,170 | 5/1993 | Press | 128/204.18 |
| 5,315,990 | 5/1994 | Mondry | . |
| 5,398,676 | 3/1995 | Press et al. | 128/204.23 |
| 5,520,170 | 5/1996 | Laswick et al. | 128/204.18 |
| 5,676,135 | 10/1997 | McClean | 128/205.22 |
| 5,735,268 | 4/1998 | Chua et al. | 128/204.23 |

*Primary Examiner*—John G. Weiss
*Assistant Examiner*—Joseph F. Weiss, Jr.
*Attorney, Agent, or Firm*—Hudak & Shunk Co., L.P.A.

[57] ABSTRACT

A portable oxygen conserving apparatus to deliver oxygen to a patient generally only during inhalation. The device includes an inlet connected to an oxygen source, an outlet which communicates oxygen to a patient, a mass-flow sensor connected to the outlet for detecting inhalation of a patient, and a valve disposed between the inlet, and outlet for controlling oxygen to the patient in response to inhalation detection and thereby providing a pulse of oxygen.

10 Claims, 6 Drawing Sheets

OXYGEN CONSERVING DEVICE

BACKGROUND OF THE INVENTION

The present invention is directed to a portable, battery powered device used to supply or deliver oxygen to a patient or user. Known devices and systems provide a continuous flow of oxygen from a regulated oxygen source. For example, a pressurized container of oxygen includes an adjustable valve that provides a continuous flow of oxygen gas to the patient. The flow rate can be adjusted but, once set, the system is intended to provide a continuous flow.

A patient, of course, does not continuously inhale so that a portion of the oxygen provided under a continuous flow system is not actually used by the patient. Other manufacturers, therefore, have developed oxygen conserving devices that provide a pulse or dose of oxygen. For example, the following U.S. patents are generally related to these types of structures: U.S. Pat. Nos. 3,923,056; 4,462,398; 4,570,631; 4,706,664; 4,823,788; 4,873,971; 4,932,402; 5,005,570; 5,038,770; and 5,315,990. Many of these alternative arrangements are simply too complex, expensive, or inadequate so that a need exists for a simple, economical, and effective device that controls oxygen supply to a user, and that allows the user to easily convert the device from a pulse mode operation to a continuous flow mode without difficulty or attendant complexity or cost associated with the device.

SUMMARY OF THE INVENTION

The subject invention is intended to conserve oxygen by permitting gas flow only during inhalation by the patient.

According to a preferred aspect of the invention, an oxygen conserving device includes an inlet connected to an oxygen source, an outlet that communicates oxygen to a patient, a mass flow sensor connected to the outlet for detecting a patient's inhalation, and a valve disposed between the inlet and outlet for controlling oxygen to the patient in response to inhalation detection and thereby providing a pulse of oxygen.

According to another aspect of the invention, the valve can be manually switched from a pulse mode to a continuous flow mode.

According to yet another aspect of the invention, the valve remains open for a predetermined period of time, for example, approximately one second, and the valve will not operate for a lock-out period after a pulse of oxygen has been delivered to the patient.

A principal advantage of the invention is a compact device that conserves oxygen by providing oxygen only after detecting inhalation.

Another advantage of the invention is the ability to easily switch between a pulse mode and continuous flow mode.

Yet another advantage of the invention resides in various visual and audible alarm features that apprise the user of the operation of the device.

Still other features and benefits of the invention will become apparent upon a reading and understanding of the detailed description.

BRIEF DESCRIPTION OF THE DRAWINGS

The invention may take physical form in certain parts and arrangements of parts, a preferred embodiment of which will be described in detail in this specification and illustrated in the accompanying drawings.

DETAILED DESCRIPTION OF THE PREFERRED EMBODIMENT

Figure 1:
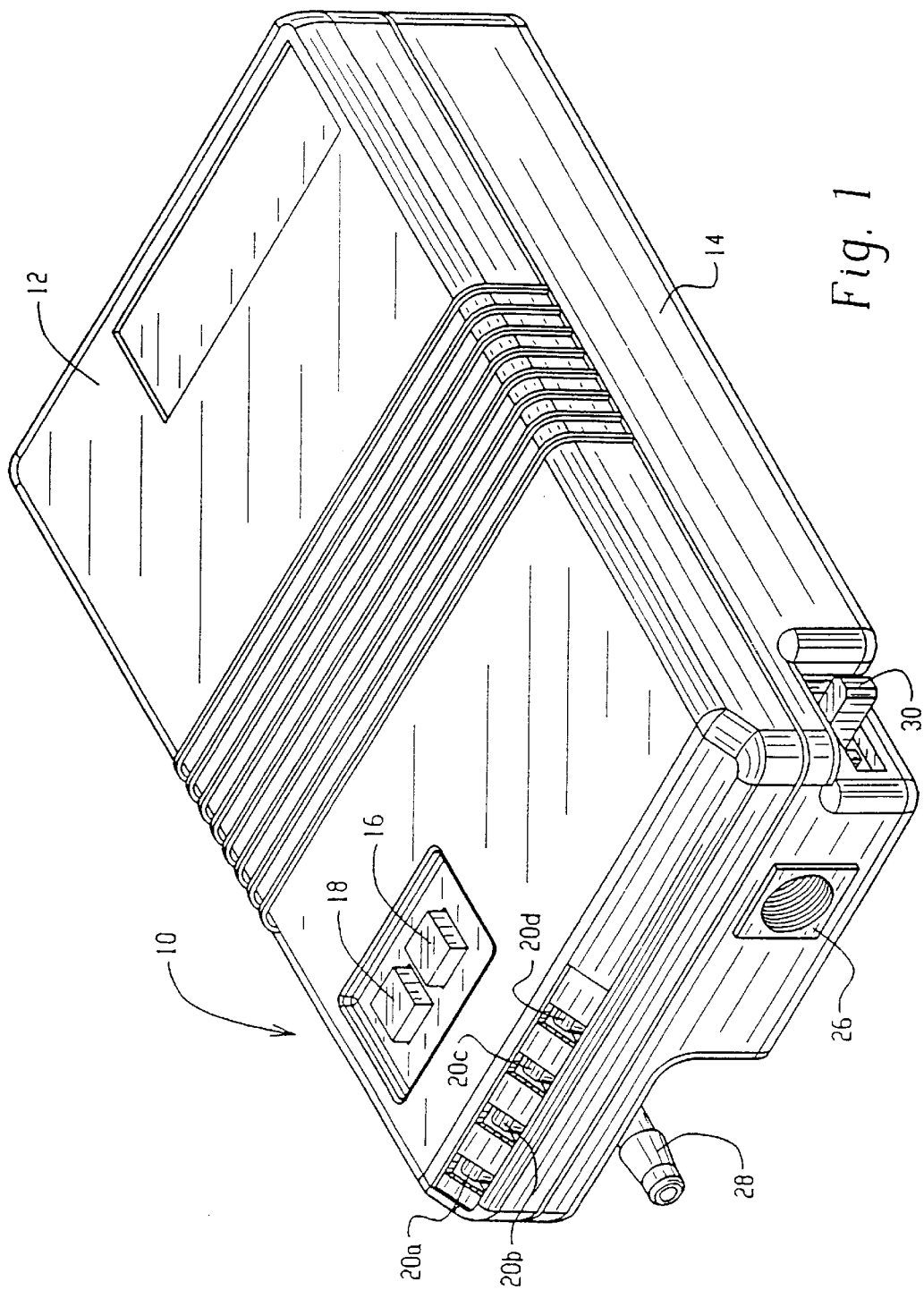
FIG. 1 is a perspective view of the demand oxygen conserving device.
Figure 2:
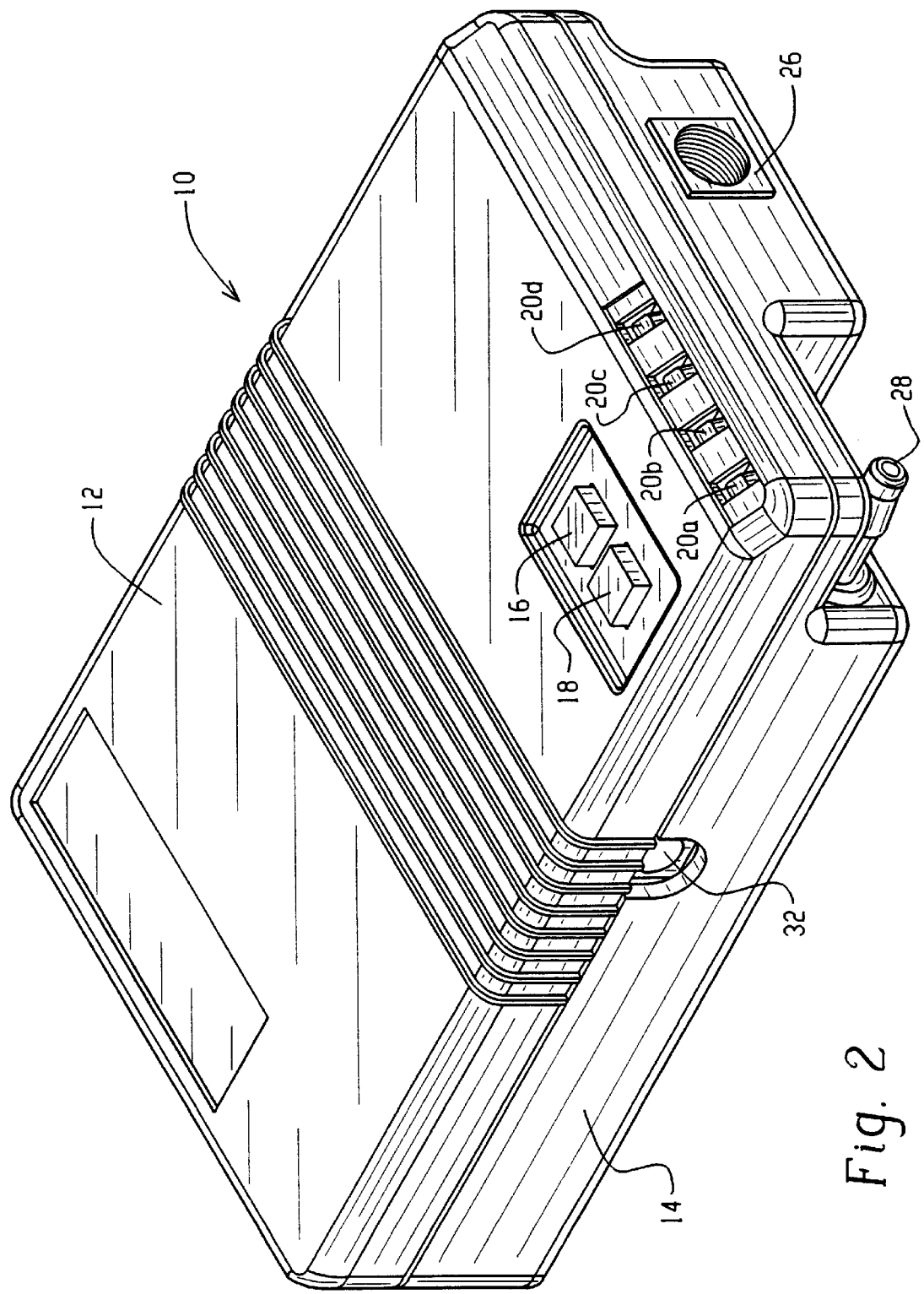
FIG. 2 is a perspective view from the opposite side of the demand oxygen conserving device.

A portable, battery powered, electrically operated, demand oxygen conserving device 10 is shown assembled in FIGS. 1 and 2. It includes a housing comprised of a first or upper housing portion 12 and a second or lower housing portion 14. Preferably, the housing is made of a flame retardant thermoplastic that is sufficiently sturdy to withstand impact loads if the device is inadvertently dropped. A series of controls and indicating features are provided on the device. For example, individual controls are provided for "pulse on" 16 and a "pulse off" 18 operation of the device. As will become more evident below these controls are designed to turn the power on and off, i.e., connect a rechargeable battery pack to a printed circuit board and solenoid valve, again, particulars of which will be described in greater detail.

Indicators such as a series of light emitting diodes (LED)s 20 are also provided on the housing. As shown, four LEDs 20a, 20b, 20c, and 20d are spaced along a peripheral portion of the upper housing. Of course, one skilled in the art will recognize that a greater or lesser number of indicators may be used depending on what features and information are to be conveyed to the patient.

An inlet 26 extends through the housing, particularly shown as extending through an end wall of the lower housing portion 14. The inlet is adapted to receive a fluid line (not shown) that extends from an oxygen source such as a pressurized tank of oxygen. A regulator valve is typically located at the outlet of the pressurized oxygen supply to provide a preselected, continuous flow of oxygen to the inlet 26. An outlet 28 is shown with a tapered or barbed configuration so that it is capable of receiving a fluid line that extends to the patient. The outlet provides pulsed oxygen flow or continuous flow to the patient, depending on the mode of operation of the device.

Additionally, a lever 30 (FIG. 1) extends outwardly from the housing and is adapted for movement between first and second positions. The lever is sized to be easily manipulated by a finger of a patient/user, and further details of the lever and switching arrangement will be described below.

An additional opening 32 (FIG. 2) is also provided in the housing and is capable of receiving an adaptor plug (not shown). The adaptor plug, when connected to an electrical outlet, provides for a rapid or quick charge of the rechargeable batteries, such as nickel cadmium batteries, that operate the device 10.

Figure 3:
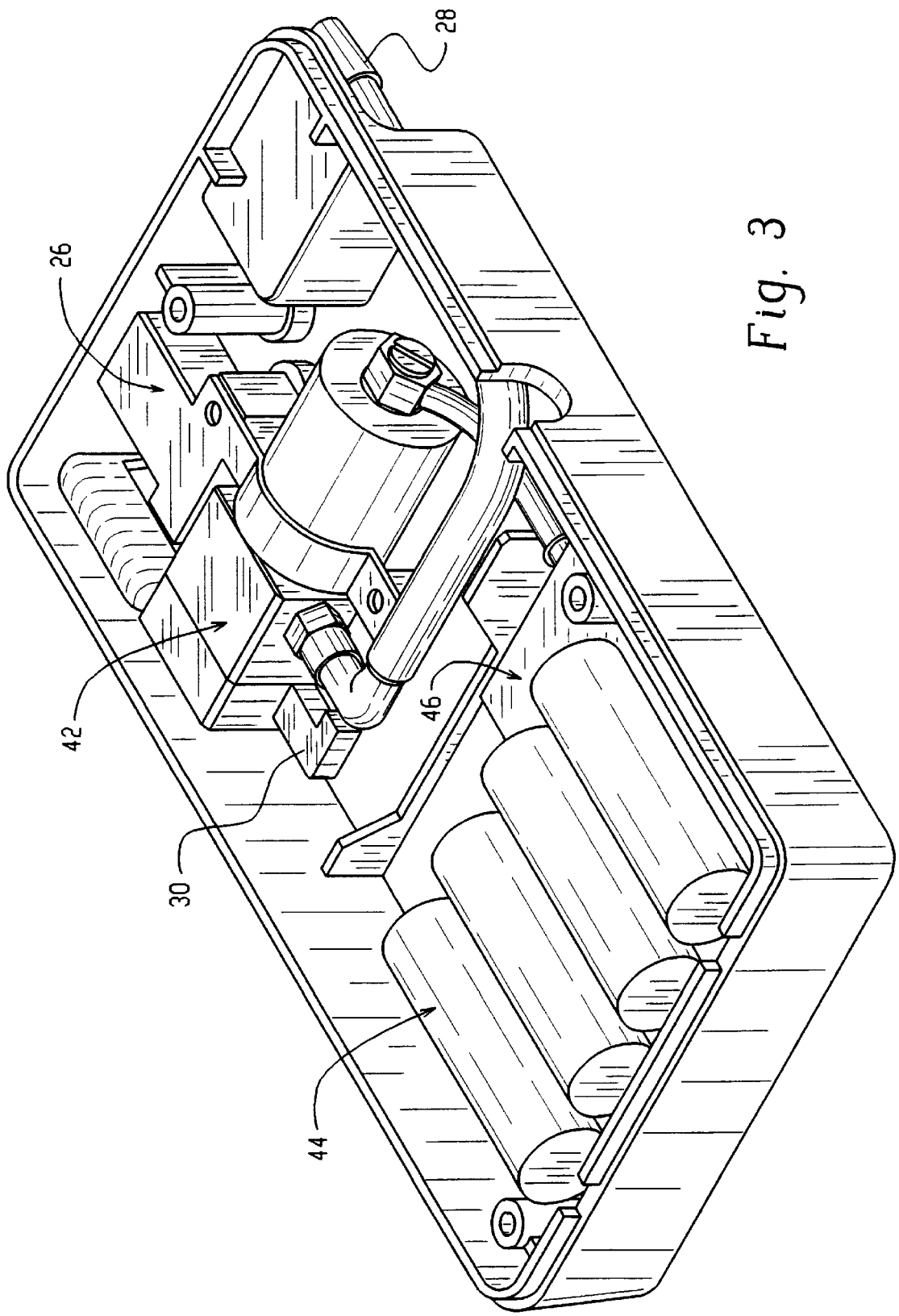
FIG. 3 is a perspective view of the demand oxygen conserving device with a top housing portion removed and illustrating various internal components.
Figure 4:
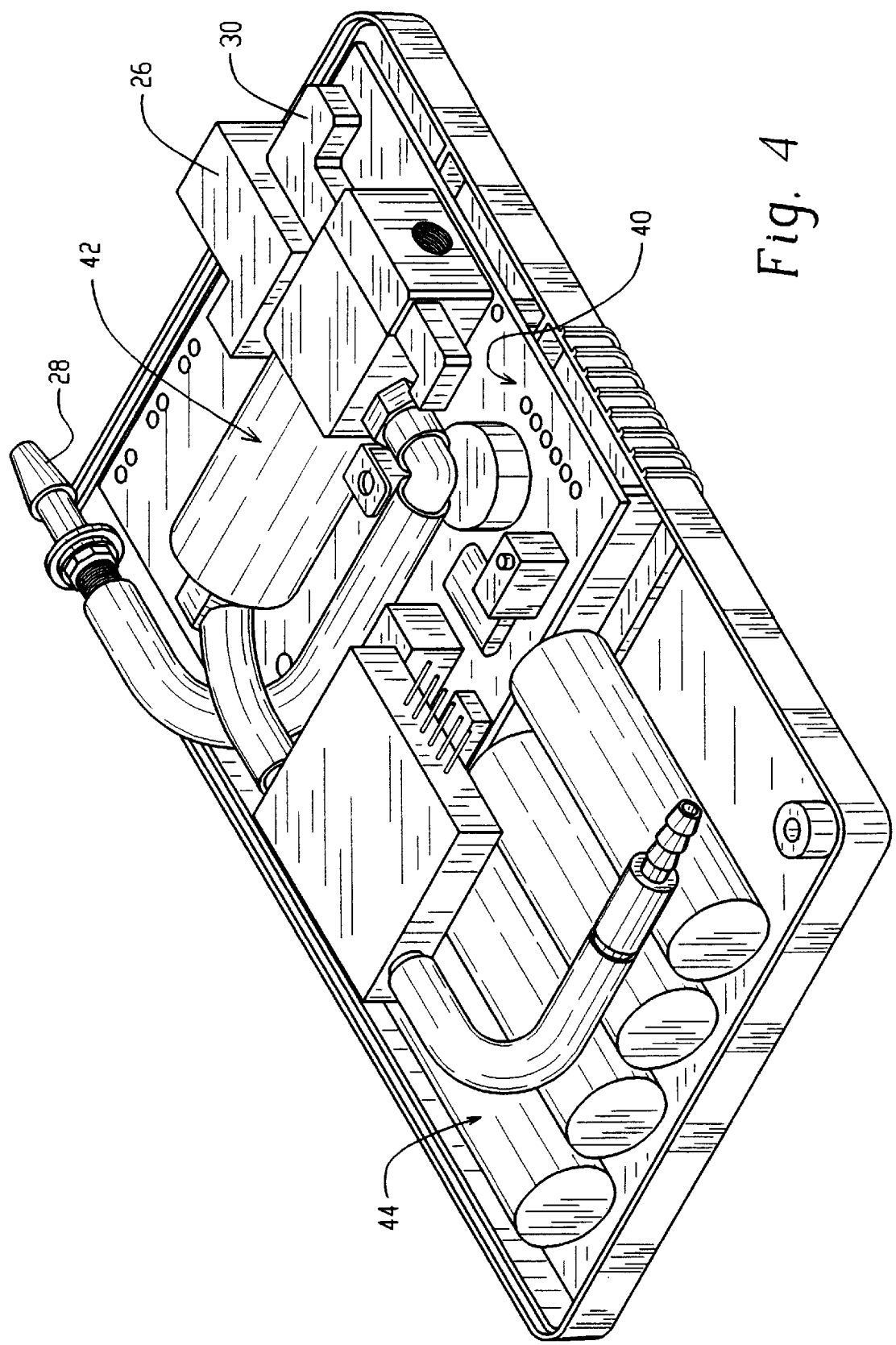
FIG. 4 is a perspective view of the device with a bottom housing portion removed.
Figure 5:
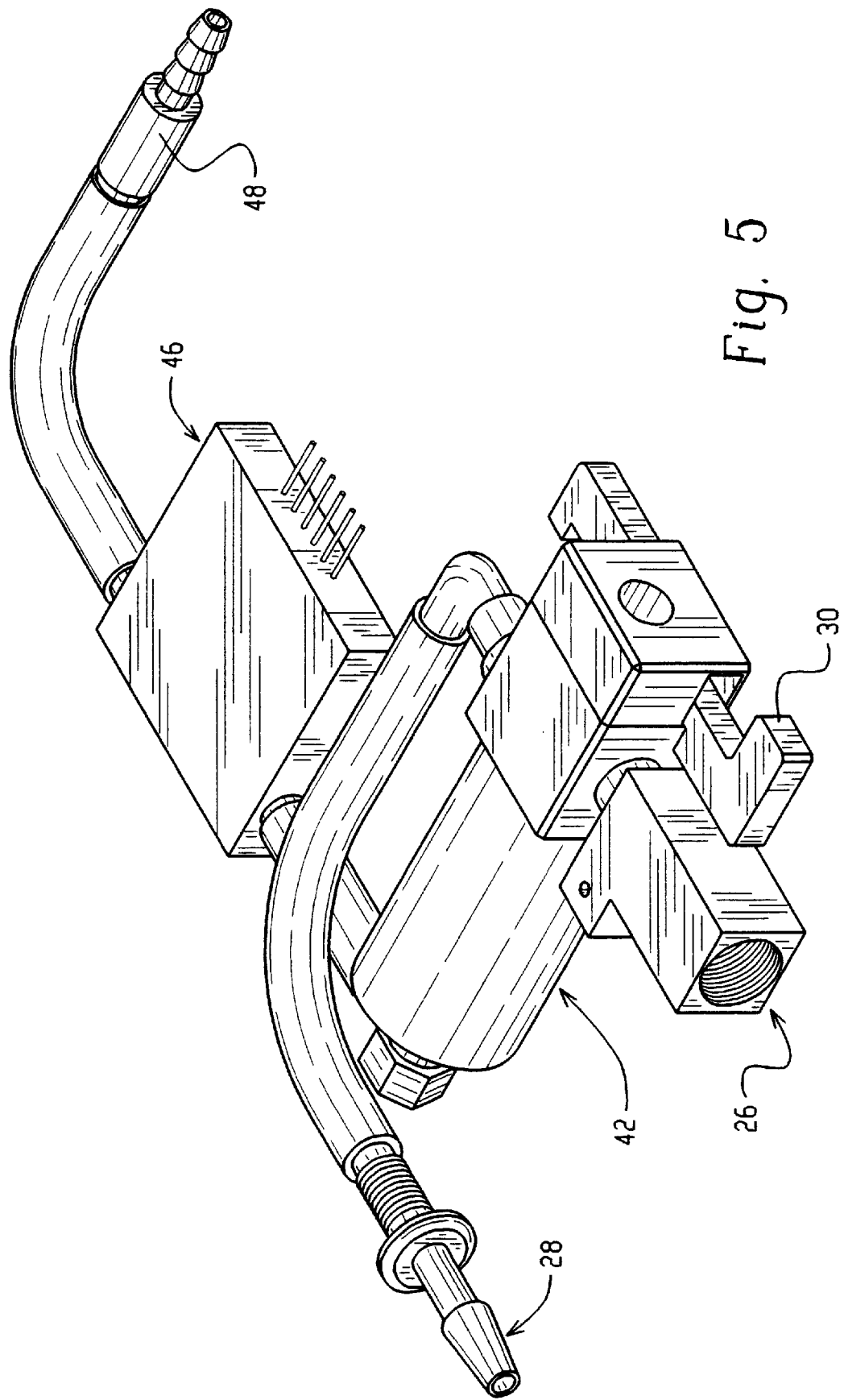
FIG. 5 is a perspective view of the internal components with both the upper and lower portions of the housing removed.

With continued reference to FIGS. 1 and 2, and additional reference to FIGS. 3–5, still other components of the demand oxygen conserving device will be described in greater detail. A printed circuit board 40 (FIG. 4) is enclosed within the housing and is electrically connected to the solenoid valve 42, rechargeable batteries 44, mass flow sensor 46, and mode switch 30. A clock circuit is provided on the circuit board to control the preselected pulse periods, preferably at one second, in response to detection of inhalation. Still other pulse periods than one second can be used without departing from the scope and intent of the subject invention. Each of the indicator LEDs is also connected to the printed circuit board to provide an appropriate signal, for example, when a pulse flow is delivered, a low battery condition is detected, the batteries are being recharged, or a default pulse is detected. Selected ones of these visual signals may be combined with an audible signal also controlled through appropriate connection to the printed circuit board.

Moreover, the solenoid valve interfaces with the printed circuit board to control oxygen flow from the inlet to the outlet. Preferably, when the solenoid is de-energized, the outlet fitting is connected to the mass air flow sensor 46. Since the solenoid valve 42 is normally closed, no oxygen from the inlet fitting reaches the outlet fitting through oxygen conserving device. Instead the patient/user's breathing is detected by the mass flow sensor due to the interconnection established between these components in the de-energized position of the valve. Particularly, air flow through an intake filter 48 (that communicates with atmosphere) is detected by the mass flow sensor that is operatively associated with the printed circuit board, and thus operatively associated with the solenoid valve. Once a breath is detected and the solenoid is energized, the outlet fitting 28 is connected to the inlet fitting 26 and the mass air flow sensor is disconnected. This description is applicable when the lever 30 is positioned in the pulse mode. Continuous flow is provided from the source to the inlet, and when inhalation is detected by the sensor 46, the solenoid is energized and provides a pulse flow between the inlet and the outlet, i.e. from the device to the patient.

Figure 6:
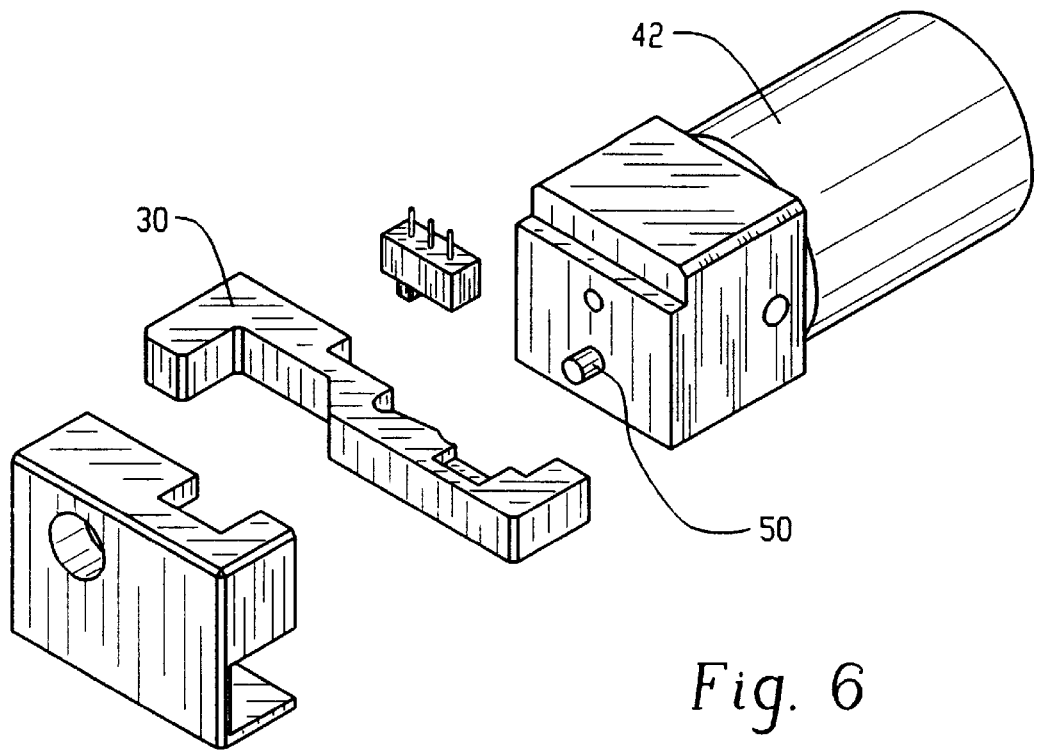
FIG. 6 is an exploded view of a manually actuated switch lever and a solenoid valve used in the demand oxygen conserving device.

When the lever 30 is switched to the second position, or continuous flow mode, contact is either made or broken with the poppet of the solenoid, or alternately the circuit board, upon manual actuation of the switch (FIG. 6). This contact disconnects the electronics so that pulse mode operation does not occur. Instead, a continuous flow of oxygen is provided to the outlet and the device 10 does not interrupt or alter the flow from the source. Instead, the flow rate is controlled at the adjustable regulator valve at the source. Accordingly, with a single valve in the device 10, multiple operations are achieved to provide a pulse flow or a continuous flow as desired.

Figure 7:
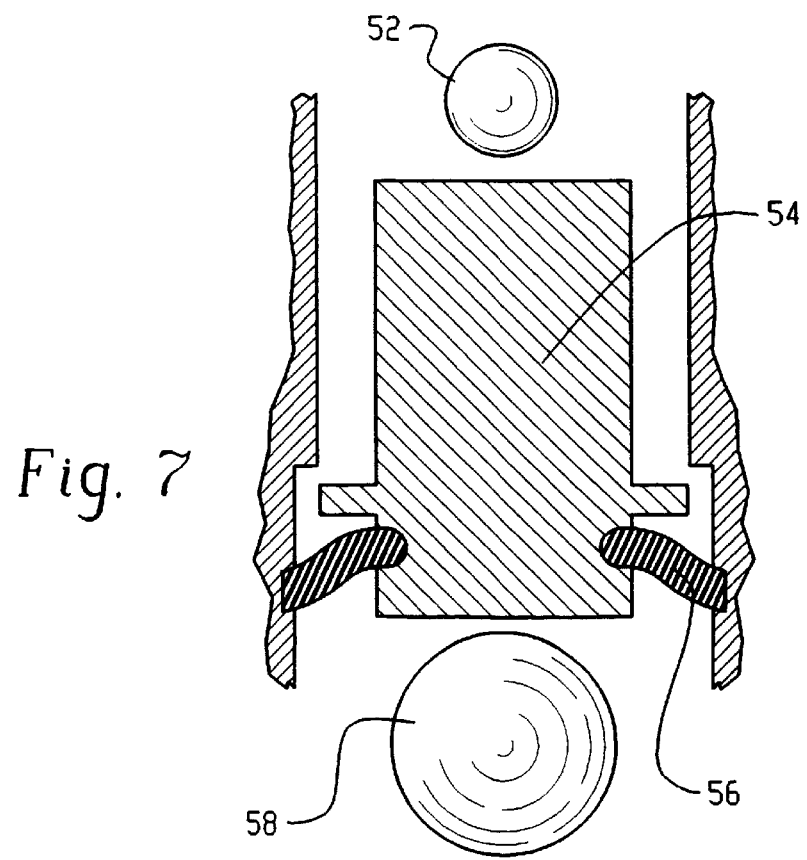
FIG. 7 is a schematic representation of a movable pin assembly that cooperates with the lever to transfer actuating movement to a poppet in the valve.

A preferred form of actuating pin is shown in greater detail in FIGS. 6 and 7. Specifically, pin 50 extends outwardly from one end of the solenoid valve. The pin is adapted to abuttingly engage a portion of the lever 30, shown in the drawings as a pair of ramped surfaces on the lever. Depending on which surface of the lever is contacting the pin 50, the pin is actuated to change the solenoid valve from an energized to a non-energized state, or vice versa, and change the oxygen conserving device from a pulse mode to a continuous flow mode, or vice versa, as desired. In a preferred configuration, a ball 52 is provided at one end of movable pin 54. The pin and ball are urged outwardly toward abutting engagement with the lever. The pin is preferably sealed about its periphery by, for example, a flexible diaphragm 56 which can also provide an outward biasing force to the assembly. A second ball 58 abuttingly engages the opposite end of the movable pin 54. Thus, sliding movement of the lever relative to the pin assembly is accommodated at end 52 which is transferred into reciprocating motion of the pin 54, which in turn is transferred to the ball 58. This allows the lever to easily actuate the valve poppet and/or establish electrical contact to the printed circuit board for desired switching.

Thus in summary, and from an operational standpoint, the mass flow sensor detects patient inhalation by sensing flow through the mass flow sensor. In response, the solenoid valve opens for a fixed period of time, preferably one second. Accordingly, the valve is quick-acting in response to patient inhalation and opens the passageway leading from the regulator associated with the source of oxygen. While the valve is open, the flow rate of oxygen is essentially constant. A prescription level or desired flow rate is set at the source tank. For example, a patient having a pulse prescription of two liters per minute (LPM) will be delivered a flow rate of two liters per minute for a period of one second. Thereafter, the valve closes until another inhalation is detected by the sensor. At a breathing rate of forty breaths per minute (BPM), a patient inhales, on average, approximately once every six seconds. Thus, a substantial conservation of oxygen gas is achieved by supplying flow only in response to inhalation.

Moreover, the conservation of oxygen is also achieved even if the pulse duration is greater or less than one second, or is variable. Since the pulse of oxygen is based on the breathing rate, a substantial conservation of oxygen is achieved when compared to continuous flow arrangements and the device comes closer to delivering oxygen only during inhalation.

As described, a pulse of oxygen is provided whenever the mass flow sensor detects patient inhalation. There is a high end lockout feature, however, that closes the valve for a set period of time in which no pulse of oxygen is available if too many pulses have occurred. The valve may be closed, for example, for a period of 0.4 seconds if the high end of a predetermined frequency range is met. These features can be programmed into the software associated with the printed circuit board to control the operation of the oxygen conserving device.

Where other flow devices of this type default to a continuous flow mode if the electronics are interrupted or a patient inhalation is not sensed, the present device will simply maintain a no-flow condition and provide an alarm signal. The alarm is preferably audible and/or visual. The preferred embodiment uses a warning light such as a continuously illuminated LED if a malfunction in the electronic controls is detected. The warning light can be used in conjunction with an audible alarm if so desired.

Still other alarm features are provided with the present invention. For example, a separate LED is illuminated upon each pulse delivery. Another LED can be illuminated during recharge of the battery pack. Yet another LED can indicate battery status. A preferred arrangement uses two different modes of intermittent and continuous illumination combined with a pattern of audible beeps to represent the condition of the batteries.

Yet another important feature is the manually operated switch to provide selective control of the oxygen flow and easily switch from a continuous flow to a pulsed flow mode, or vice versa. In the pulsed flow position, a pulse flow of oxygen is provided whenever inhalation is detected, and in a manner as described above. By manually altering the position of the switch, the device provides for continuous flow. Additionally, the switch is integral to the valve and of simplified, reliable structure. All of this is achieved with a single solenoid valve in which the oxygen inlet line is normally closed and the oxygen outlet line is normally open. This greatly simplifies the structure and allows the above-described operation to be achieved.

The invention has been described with reference to the preferred embodiment. Obviously, modifications and alterations will occur to others upon a reading and understanding of this specification. It is intended to include all such modifications and alterations insofar as they come within the scope of the appended claims or the equivalents thereof.

Having thus described the invention, it is now claimed:

1. A portable oxygen conserving device adapted to control the flow of oxygen from a source to a patient, comprising:

a housing;

said device having an inlet adapted for connection with an oxygen source;

said device having an outlet adapted for communicating oxygen to a patient;

said device having at least one battery;

said device having a mass flow sensor within said housing in operative communication with the outlet for detecting a patient's inhalation;

said device having a valve with an electronic control, said valve and said electronic control being powered by said battery and all being contained within said housing said valve being interposed between the inlet and outlet for controlling the flow of oxygen from the inlet to the outlet in response to the mass flow sensor detecting a patient's inhalation and providing a pulse of oxygen to the patient, wherein said valve is energized by said control to an open state whereby said inlet and said outlet are in continuous fluid communication and said valve is de-energized by said control to a closed state whereby fluid communication between said inlet and said outlet is precluded; and said device having a manual switch for switching said valve between a pulse mode and a continuous flow mode to provide a continuous flow of oxygen to a patient.

2. The device as defined in claim 1 wherein the manual switching member includes a lever that is operatively associated with a poppet of the valve for switching the valve from a normally closed position in which the outlet does not communicate with the inlet to an open position where the inlet and outlet are in constant communication.

3. The device as defined in claim 1 wherein the valve is a solenoid operated valve that is connected to a printed circuit board and maintains the valve open for a predetermined period in response to the mass flow sensor detecting inhalation, wherein said valve is energized when said valve is open.

4. The device as defined in claim 3 wherein the predetermined period is approximately one second.

5. The device as defined in claim 3 wherein the valve will not operate for a lockout period after a pulse of oxygen has been delivered to the patient.

6. The device as defined in claim 1 further comprising alarm features indicating at least one of no-flow condition, electronic interruption, pulse delivery, battery recharge, and battery status.

7. A portable oxygen conserving device adapted to control the flow of oxygen from a pressurized oxygen tank to a patient, comprising:

a housing;

said device having an inlet adapted for connection with an oxygen source;

said device having an outlet adapted for communicating oxygen to a patient;

said device having at least one rechargeable battery;

said device having a mass flow sensor within said housing operatively connected to said outlet for detecting a patient's inhalation; and said device having a valve, said valve being powered by said battery and being contained within said housing said valve being normally closed and in a de-energized state precluding the flow of oxygen between said inlet and said outlet; and said device having a manual switch for switching said valve between a pulse mode and a continuous flow mode to provide a continuous flow of oxygen to a patient and said device further monitoring the condition of said battery and providing a signal to said patient when a low battery condition is detected whereby said patient is warned to activate said manual switch in order to assure a continuous flow of oxygen.

8. The oxygen conserving device of claim 7, wherein said valve is a solenoid valve which is operatively connected to a circuit board and wherein said valve, when in an energized state, maintains the valve open for a predetermined period in response to the mass flow sensor detecting inhalation.

9. The oxygen conserving device of claim 8, wherein said predetermined period is approximately one second.

10. The oxygen conserving device of claim 9, wherein said device maintains a no flow condition and provides an alarm signal, either audible or visual, when either the electronics is interrupted or a patient inhalation is not sensed.

* * * * *